(12) United States Patent
Takahashi et al.

(10) Patent No.: US 6,567,114 B2
(45) Date of Patent: May 20, 2003

(54) VIDEO-SIGNAL PROCESSING DEVICE CONNECTABLE TO AN ELECTRONIC ENDOSCOPE

(75) Inventors: Akihiro Takahashi, Tokyo (JP); Kouhei Iketani, Tokyo (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 10/114,300

(22) Filed: Apr. 3, 2002

(65) Prior Publication Data

US 2002/0145661 A1 Oct. 10, 2002

Related U.S. Application Data

(62) Division of application No. 08/833,254, filed on Apr. 4, 1997, now Pat. No. 6,466,256.

(30) Foreign Application Priority Data

Apr. 5, 1996 (JP) ............................................. 08-110269
Apr. 15, 1996 (JP) ............................................. 08-117086

(51) Int. Cl.[7] ................................................. H04N 7/18
(52) U.S. Cl. ....................................................... 348/71
(58) Field of Search ........................ 250/201.9; 348/45, 348/65, 68–74, 76, 222.1; 600/101, 109; 601/3; 606/205; H04N 7/18

(56) References Cited

U.S. PATENT DOCUMENTS

| 4,716,457 | A |   | 12/1987 | Matsuo |   |
|---|---|---|---|---|---|
| 4,746,975 | A | * | 5/1988 | Ogiu | ............................ 348/76 |
| 4,853,772 | A |   | 8/1989 | Kikuchi |   |
| 4,924,856 | A |   | 5/1990 | Noguchi |   |
| 4,950,880 | A |   | 8/1990 | Hayner |   |
| 5,138,458 | A |   | 8/1992 | Nagasaki et al. |   |
| 5,255,669 | A | * | 10/1993 | Kubota et al. | .................. 601/3 |
| 5,305,098 | A |   | 4/1994 | Matsunaka et al. |   |
| 5,374,953 | A |   | 12/1994 | Sasaki et al. |   |
| 5,696,553 | A |   | 12/1997 | D'Alfonso et al. |   |
| 5,864,361 | A |   | 1/1999 | Sekiya et al. |   |
| 5,877,802 | A |   | 3/1999 | Takahashi et al. |   |
| 5,902,230 | A |   | 5/1999 | Takahashi et al. |   |
| 5,929,899 | A |   | 7/1999 | Takahashi et al. |   |
| 6,068,647 | A | * | 5/2000 | Witt et al. | ................... 606/205 |
| 6,215,517 | B1 |   | 4/2001 | Takahashi |   |
| 6,319,198 | B1 |   | 11/2001 | Takahashi |   |

* cited by examiner

Primary Examiner—Richard Lee
(74) Attorney, Agent, or Firm—Greenblum & Bernstein, P.L.C.

(57) ABSTRACT

A video-signal processing device connectable to an electronic endoscope capable of outputting a component-type electric analog color video signal. An analog-to-digital converter converts video-signal components of the component-type video signal into parallel digital color video-signal components. A color-conversion digital matrix circuit produces a parallel digital luminance signal-component, and two kinds of parallel digital color-difference signal-components based on the parallel digital color video-signal-components. A parallel-to-serial converter converts the luminance signal-component and digital color-difference signal-components into serial digital color video-signal-components. The electric analog video signal outputted from the electronic endoscope is fed outside the device as the serial electric digital video signal.

6 Claims, 14 Drawing Sheets

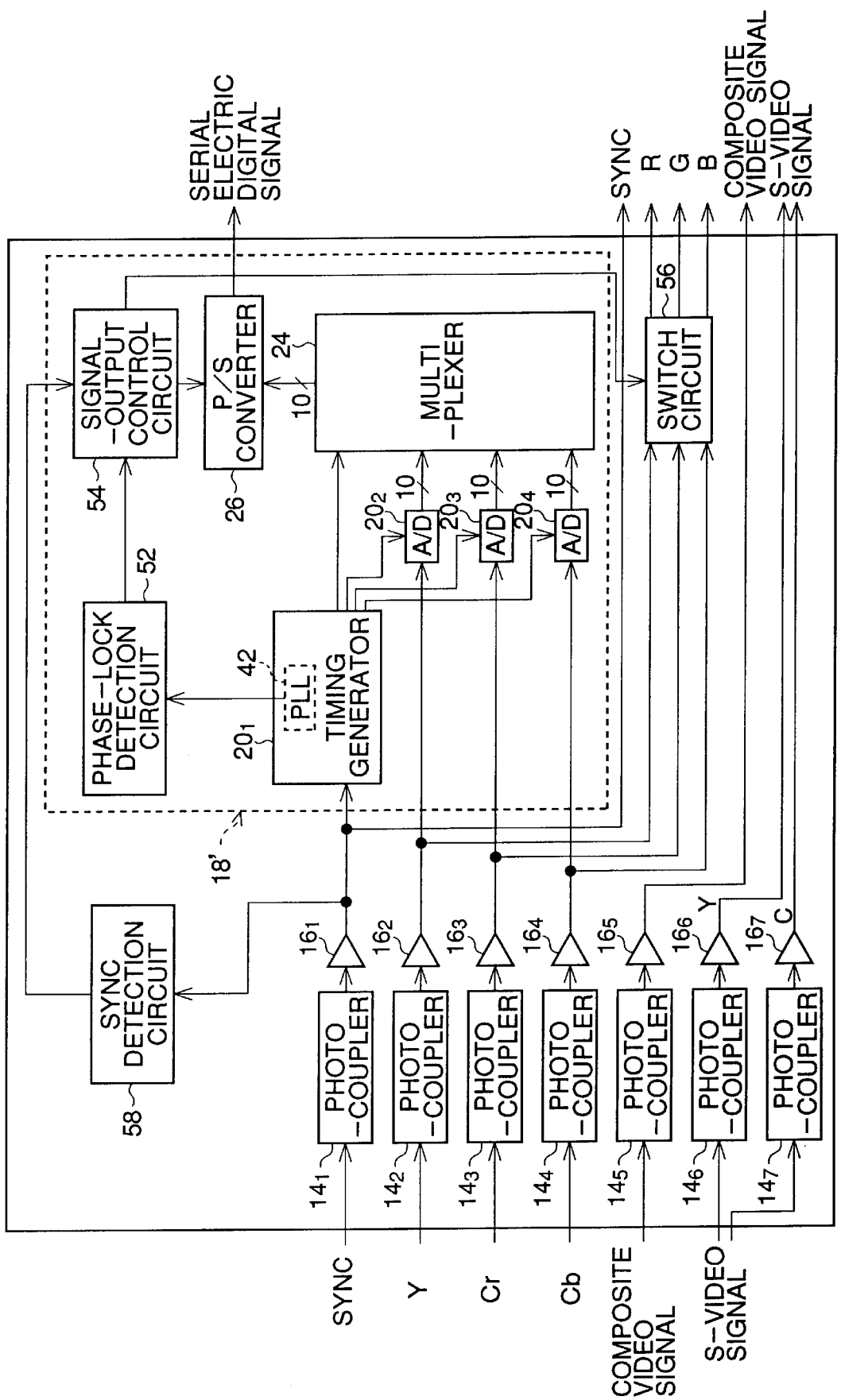

VIDEO-SIGNAL PROCESSING DEVICE CONNECTABLE TO AN ELECTRONIC ENDOSCOPE

CROSS-REFERENCE TO RELATED APPLICATIONS

This is a divisional of U.S. application Ser. No. 08/833,254, filed Apr. 4, 1997, now U.S. Pat. No. 6,446,256, the entire disclosure of which is expressly incorporated by reference herein in its entirety.

BACKGROUND OF THE INVENTION

1. Field of the Invention

The present invention relates to a video-signal processing device which is connectable to an electronic endoscope, and more particularly relates to a video-signal processing device intervened between an electronic endoscope and peripheral equipments such as a television (TV) monitor, a video tape recorder, a printer, a video-image processing computer, and so on.

2. Description of the Related Art

Such an electronic endoscope comprises a flexible conduit and a video processor to which the flexible conduit is detachably joined.

The flexible conduit has an objective lens system provided at the distal end thereof, and a solid image sensor such as a CCD (charge-coupled device) associated therewith. An object to be photographed is focussed, as an optical image, on a light receiving surface of the CCD image sensor by the objective lens system. The optical image is converted into analog image-pixel signals by the CCD image sensor, and the analog image-pixel signals are successively read out of the image sensor by a CCD driver circuit therefor.

Also, the flexible conduit has an optical guide provided therewithin, and the optical guide terminates at a light-emitting end face at the distal end of the flexible conduit. The video processor includes an optical guide provided therein. When the flexible conduit is joined to the video processor, one end of the optical guide of the video processor is connected to a proximal end of the optical guide of the flexible conduit.

The video processor of the electronic endoscope also has a light source, and a collective lens system associated therewith, and light rays emitted from the light source are focussed on the other end face of the optical guide of the video processor by the collective lens system. Thus, a front area of the distal end of the flexible conduit is illuminated by the light rays emitted from the light-emitted end face of the optical guide of the flexible conduit.

For reproduction of a photographed image as a color image, for example, an RGB field sequential type color imaging system is introduced in the electronic endoscope. Namely, a rotary RGB color filter is intervened between the light source and the inner end face of the optical guide of the video processor, and the RGB color filter is rotated at a given frequency of rotation, whereby an object to be photographed is sequentially illuminated by red light rays, green light rays, and blue light rays. Thus, a red optical image, a green optical image, and a blue optiacal image are focussed on the light receiving surface of the CCD image sensor at given time intervals.

Analog color-image-pixel signals successively read from the CCD image sensor by the CCD driver circuit are fed to the video processor, which processes the analog color-image pixel signals to thereby produce a color video signal.

Usually, the video processor of the electronic endoscope is connected to a medical TV monitor designed to ensure electrical security, and a photographed image is reproduced on the medical TV monitor on the basis of the color video signal fed from the video processor thereto.

Also, the electronic endoscope may be connected to a TV monitor on the market at medical site for reproduction of a photographed image thereon, but in general the TV monitor on the market is not designed to ensure electrical security.

On the other hand, there is a demand for connecting an electronic endoscope to other peripheral equipments (such as a video tape recorder, a printer, an image-processor and so on) other than a TV monitor. To this end, the video processor of the electronic endoscope is arranged so as to output at least two kinds of color video signals. However, in this case, of course, the peripheral equipments are not designed to ensure electrical security.

Furthermore, there is a demand for connecting the electronic endoscope to a peripheral equipment remotely located from where the electronic endoscope is used. For example, at a large hospital of more than two buildings, there may be a case where a color video signal must be fed from the electronic endoscope used at a room of a building to a peripheral equipment located at a room of another building. In this case, the video signal should be fed as a digital video signal from the electronic endoscope to the peripheral equipment, because an analog video signal is susceptible to attenuation.

Nevertheless, the feeding of the digital video signal to the remote peripheral equipment is not expedient, because an expensive signal cable having at least plural signal lines corresponding to a bit number of the digital video signal must be laid therebetween.

SUMMARY OF TEE INVENTION

Therefore, an object of the present invention is to provide a video-signal processing device connectable to an electronic endoscope such that at least one kind of video signal is fed as a serial digital signal from the electronic endoscope to a peripheral equipment such as a TV monitor, a video tape recorder, a printer, an image-processor and so on therethrough, whereby the feeding of the video signal from the electronic endoscope to the peripheral equipment is possible without using an expensive signal cable having a plurality of signal lines.

Another object of the present invention is to provide a video-signal processing device of the above-mentioned type, wherein a feeding of uncontrollable image the video signal to the peripheral equipment can be prevented during the connection of the video-signal processing device to the electronic endoscope.

Yet another object of the present invention is to provide a video-signal processing device of the above-mentioned type, wherein a feeding of image the video signal to the peripheral equipment can be forcibly stopped, if necessary.

Furthermore an object of the present invention is to provide a video-signal processing device of the above-mentioned type, wherein a feeding of image the video signal to the peripheral equipment is possible in such a manner that the electronic endoscope is electrically insulated from the video-signal processing for electrical security.

In accordance with an aspect of the present invention, there is provided a video-signal processing device connectable to an electronic endoscope designed to output at least one kind of electric analog video signal, the device comprising: an analog-to-digital converter for converting the electric analog video signal into a parallel electric digital video signal; and a parallel-to-serial converter for converting the parallel electric digital video signal into a serial electric digital video signal, whereby the electric analog video signal outputted from the electronic endoscope is fed outside from the device as the serial electric digital video signal.

The video-signal processing device may further comprise: an electrical-optical converter for converting the serial electric digital video signal into a serial optical digital video signal; a manual switch for forcibly stopping the feeding of the serial electric digital video signal from the device; and a insulation coupler for making it possible to input the electric analog video signal from the electronic endoscope to the device, whereby the electronic endoscope is electrically insulated from the device. The insulation coupler may be a photo-coupler or a transformer coupler.

In accordance with another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, and at least three kinds of video-signal-components, the device comprising: an analog-to-digital converter for converting the video- signal-components into parallel electric digital video-signal-components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are outputted outside at proper timing from the device.

The video-signal processing device may further comprise: an electrical optical converter for converting the serial electric digital video-signal-components into serial optical digital video-signal-components; a manual switch for forcibly stopping the outputting of the serial video-signal-components from the device; an insulation coupler for making it possible to input the component-type electric analog color video signal from the electronic endoscope to the device, whereby the electronic endoscope is electrically insulated from the peripheral equipment.

Furthermore, the video-signal processing device may comprise: a phase-lock detector for detecting the coincidence of the phase of the clock pulses with the phase of the composite synchronizing signal; a signal-output stopper for stopping the outputting of the serial digital video-signal-components from the device until the phase-lock detector detects the coincidence of the phase of the clock pulses with the phase of the composite synchronizing signal; and an electrical-optical converter for converting the serial electric digital video-signal-components into serial optical digital video-signal-components.

In accordance with yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, a red video-signal-component, a green video-signal-component, and a blue video-signal-component, the device comprising: a color-conversion analog matrix circuit for producing a luminance signal-component, and two kinds of color-difference signal components on the basis of the read, green, and blue video-signal-components; an analog-to-digital converter for converting each of the luminance signal-component, and the two kinds of color-difference signal components into a parallel electric digital video-signal-components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are outputted outside at proper timing from the device.

In accordance with yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, a red video-signal-component, a green video-signal-component, and a blue video-signal-component, the device comprising: an analog-to-digital converter for converting each of the red, green, and blue video-signal-components into a parallel digital color video-signal-component; a color-conversion digital matrix circuit for producing a parallel digital luminance signal-component, and two kinds of parallel digital color-difference signal-components on the basis of the parallel digital color video-signal components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are outputted outside at proper timing from the device.

In accordance with yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, a luminance signal-component, and two kinds of color-difference signal components, the device comprising: an analog-to-digital converter for converting each of the luminance signal-component, and the two kinds of color-difference signal components into a parallel electric digital video-signal-components; a parallel-to-serial converter for converting the parallel digital video-signal-components into serial digital video-signal-components and for outputting the serial digital video-signal-components in accordance with a series of clock pulses; and a phase-locked loop circuit for coinciding a phase of the clock pulses with a phase of the composite synchronizing signal component of the component-type electric analog color video signal, whereby the serial digital video-signal-components are outputted outside at proper timing from the device.

In accordance with yet another aspect of the present invention, there is provided a video-signal processing device connectable to an electronic endoscope designed to output at least two kinds of video signals, the device comprising: a switch circuit provided in output-signal lines for the two kinds of video signals; and respective manual switches corresponding the two kinds of video signals for operating the switch circuit in such a manner that an outputting of one of the two kind of video signals from the device is forcibly stopped when turning ON the corresponding manual switch.

In accordance with yet another aspect of the present invention, there is provided a video-signal processing device connectable to an electronic endoscope designed to output at least one kind of video signal, and a plurality of control signals for a video image processing computer, the device comprising: an analog-to-digital converter for converting the electric analog video signal into a parallel electric digital video signal; a parallel-to-serial converter for converting the parallel electric digital video signal into a serial electric digital video signal, whereby the electric analog video signal outputted from the electronic endoscope is fed outside from the device as the serial electric digital video signal; and a processing circuit for processing a command signal, fed from the video-image processing computer to the device, for stopping the feeding of the serial electric digital video signal, whereby the feeding of the serial electric digital video signal is forcibly stopped upon receiving the command signal.

BRIEF DESCRIPTION OF THE DRAWINGS

The objects and other objects of the present invention will be better understood from the following description, with reference to the accompanying drawings in which:

FIG. 14 is a block diagram showing a sixth embodiment of the video-signal processing device according to the present invention.

DESCRIPTION OF THE PREFERRED EMBODIMENTS

Figure 1:
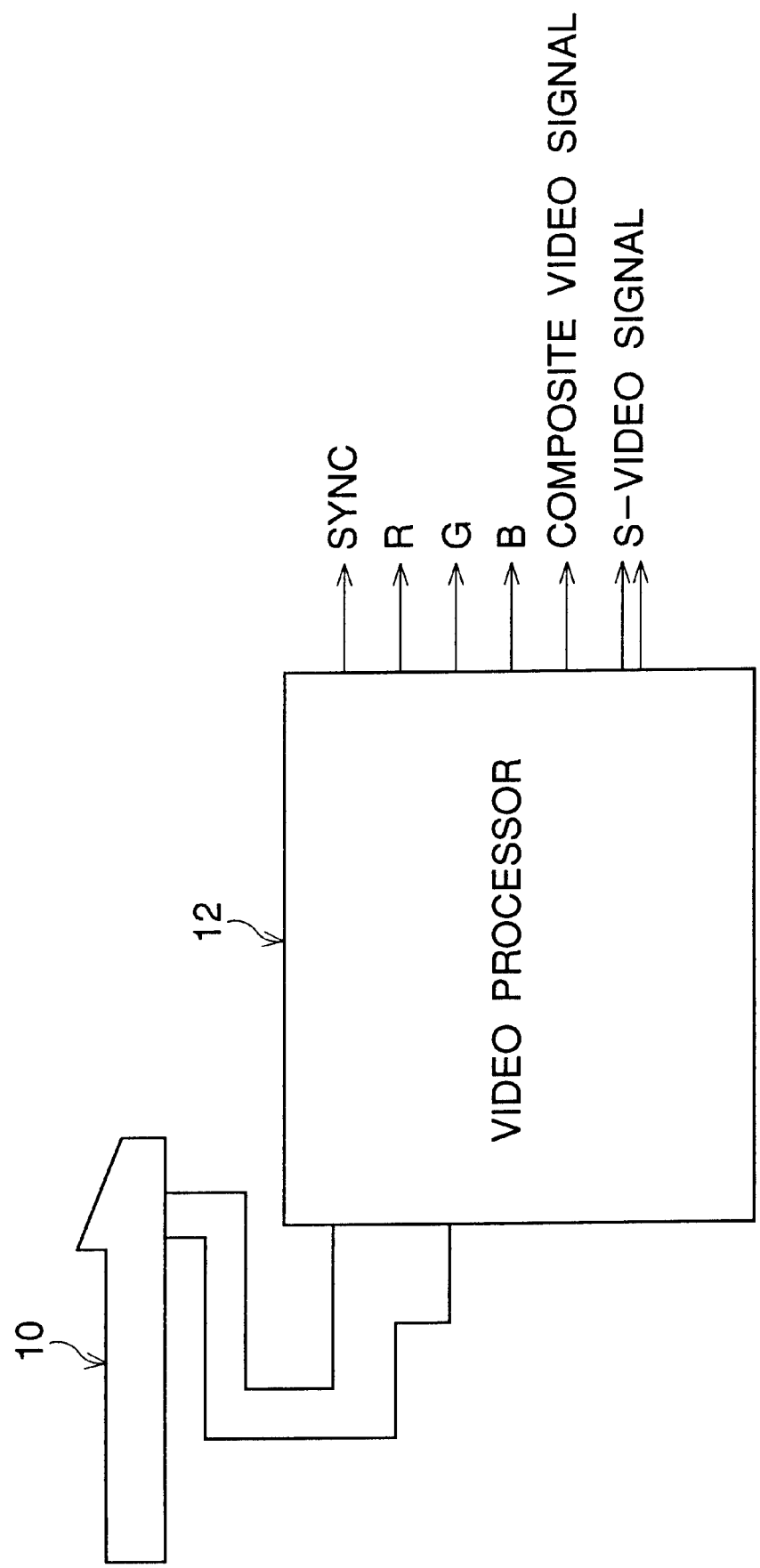
FIG. 1 is a schematic view showing an electronic endoscope to which a video-signal processing device according to the present invention may be connected.

FIG. 1 schematically shows an electronic endoscope, to which a video-signal processing device according to the present invention may be connected. The electronic endoscope comprises a flexible conduit 10, and a video processor 12 to which the flexible conduit 10 is detachably joined.

The flexible conduit 10 has an objective lens system provided at the distal end thereof, and a solid image sensor such as a CCD (charge-coupled device) associated therewith. An object to be photographed is focussed as an optical image on a light receiving surface of the CCD image sensor by the objective lens system. The optical image is converted into analog image-pixel signals by the CCD image sensor, and the analog image-pixel signals are successively read out of the image sensor by a CCD driver circuit therefor.

Also, the flexible conduit 10 has an optical guide provided therewithin, and the optical guide may be formed by a bundle of optical fibers. The optical guide terminates at a light-emitting end face at the distal end of the flexible conduit 10. On the other hand, the video processor 12 includes an optical guide provided therein, and this optical guide may be also formed by a bundle of optical fibers. When the flexible conduit 10 is joined to the video processor 12, one end of the optical guide of the video processor 12 is connected to a proximal end of the optical guide of the flexible conduit 10.

The video processor 12 also has a light source, and a collective lens system associated therewith, and light rays emitted from the light source are focussed on the other end face of the optical guide of the video processor 12 by the collective lens system. Thus, a front area of the distal end of the flexible conduit 10 is illuminated by the light rays emitted from the light-emitted end face of the optical guide of the flexible conduit 10.

For reproduction of a photographed image as a color image, for example, an RGB field sequential type color imaging system is introduced in the electronic endoscope. Namely, a rotary RGB color filter is intervened between the light source and the inner end face of the optical guide of the video processor 12, and the RGB color filter is rotated at a given frequency of rotation, whereby an object to be photographed is sequentially illuminated by red light rays, green light rays, and blue light rays. Thus, a red optical image, a green optical image, and a blue optical image are focussed on the light receiving surface of the CCD image sensor at given time intervals.

Analog color-image-pixel signals successively read from the CCD image sensor are fed to the video processor 12, and are then subjected to various image-processings such as white-balance processing, gamma-correction processing and so on. In the electronic endoscope shown in FIG. 1, three kinds of color video signals are produced on the basis of the processed color-image-pixel signals, and are outputted from the video processor 12.

Namely, as shown in FIG. 1, as a first kind of color video signal, a component-type color video signal composed of a composite synchronizing signal (SYNC), a red video signal (R), a green video signal (G), and a blue video signal (B) is outputted from the video processor 12; as a second kind of color video signal, an S-video signal composed of a luminance signal, and an amplitude-modulated (AM) color-difference signal is outputted from the video processor 12; and, as a third kind of color video signal, a composite color video signal combined with a luminance signal and an amplitude-modulated (AM) color-difference signal is outputted from the video processor 12.

Figure 2:
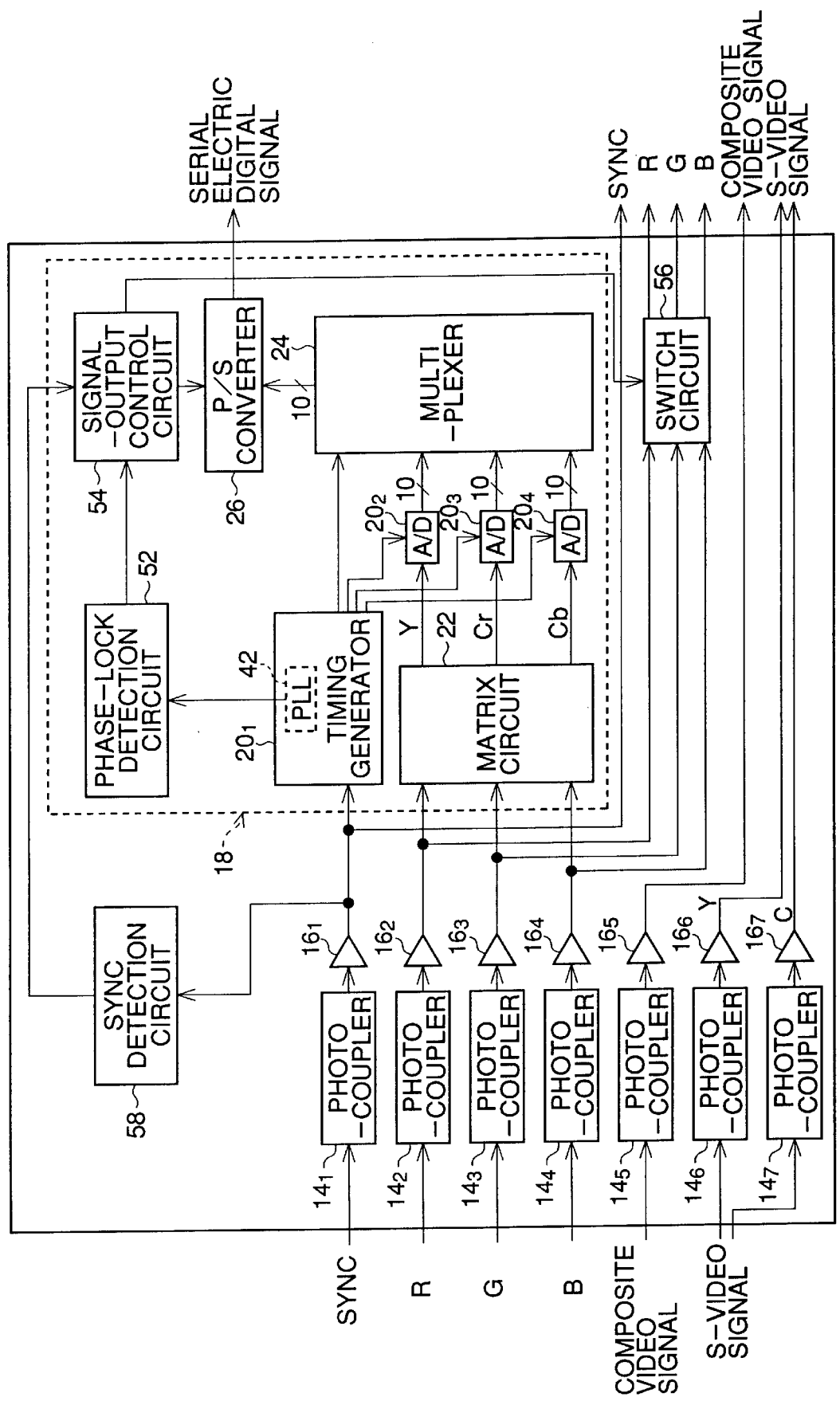
FIG. 2 is a block diagram showing a first embodiment of the video-signal processing device according to the present invention.

FIG. 2 shows a block diagram of a first embodiment of the video-signal processing device according to the present invention, which is connectable to the video processor 12 of the electronic endoscope shown in FIG. 1. The video-signal processing device comprises seven photo-couplers $14_1$ to $14_7$, and, when the video-signal processing device is connected to the video processor 12, the three kinds of video signals outputted from the video processor 12 are inputted to the seven photo-couplers $14_1$ to $14_7$.

In particular, the respective composite synchronizing signal (SYNC), red video signal (R), green video signal (G), and blue video signal (B) of the first kind of color video signal (the component-type color video signal) are inputted to the photo-couplers $14_1$ to $14_4$; the respective luminance signal and amplitude-modulated (AM) color-difference signal of the second kind of color video signal (the S-video signal) are inputted to the photo-couplers $14_6$ and $14_7$; and the third kind of color video signal, i.e., the composite color video signal combined with the luminance signal and the amplitude-modulated (AM) color-difference signal is inputted to the photo-coupler $14_5$.

Each of the photo-couplers $14_1$ to $14_7$ once converts the inputted electric signal into a photo-signal, and then outputs the photo-signal as an electric signal. Namely, the video-signal processing device is optically coupled to the video processor 12 of the electronic endoscope, whereby the electronic endoscope is electrically insulated from various peripheral equipments connected to the electronic endoscope through the video-signal processing device according to the present invention.

The respective composite synchronizing signal (SYNC), red video signal (R), green video signal (G), and blue video signal (B) outputted from the photo-couplers $14_1$ to $14_4$ are amplified by the amplifiers $16_1$ to $16_4$, and the amplified signals (SYNC, R, G, B) are inputted to a digital-conversion processing circuit 18 including a timing generator circuit $20_1$; three analog-to-digital (A/D) converters $20_2$, $20_3$, and $20_4$; a color-conversion matrix circuit 22; a multiplexer 24; and a parallel-to-serial (P/S) convertor 26.

In particular, the amplified composite synchronizing signal (SYNC) outputted from the amplifier $16_1$ is inputted to the timing generator circuit $20_1$ which produces a horizontal synchronizing signal, a vertical synchronizing signal, and several series of clock pulses having individual frequencies produced on the basis of the inputted composite synchronizing signal (SYNC).

Also, the respective amplified red video signal (R), green video signal (G), and blue video signal (B) outputted from the amplifiers $16_2$, $16_3$, and $16_4$ are inputted to the color-conversion matrix circuit 22, which produces a luminance signal (Y), and two kinds of color-difference signals ($C_r$=R−Y and $C_b$=B−Y) on the basis of the inputted color video signals (R, G, and B). Then, the luminance signal (Y), and the two kinds of color-difference signals ($C_r$ and $C_b$) are inputted to the A/D converters $20_2$, $20_3$, and $20_4$, in which the signals (Y, $C_r$, and $C_b$) are converted into 10-bit digital signals, respectively.

In this embodiment, the sampling of the 10-bit digital luminance signal (Y) from the A/D converter $20_2$ is carried out in accordance with a series of clock pulses of 13.5 MHz outputted from the timing generator circuit $20_1$. Also, the sampling of each 10-bit digital color-difference signal ($C_r$, $C_b$) from the A/D converters $20_3$ and $20_4$ are carried out in accordance with a series of clock pulses of 6.75 MHz outputted from the timing generator circuit $20_1$. Namely, the sampling frequency of the digital luminance signal is twice as many as that of each digital color-difference signal ($C_r$, $C_b$).

The 10-bit digital signals (Y, $C_r$, and $C_b$) outputted from the A/D converters $20_2$, $20_3$, and $20_4$ are inputted to the multiplexer 24, which output the 10-bit digital signals (Y, $C_r$, and $C_b$) in regular sequence. In this embodiment, for example, the outputting of the 10-bit digital signals (Y, $C_r$, and $C_b$) may be sequentially carried out in the order of the luminance signal (Y), the color-difference signal ($C_r$), the luminance signal (Y), and the color-difference signal ($C_b$). Also, the sequential outputting of the 10-bit digital signals (Y, $C_r$, and $C_b$) is based upon a series of clock pulses of 27 MHz outputted from the timing generator circuit $20_1$. Note, the frequency of 27 MHz is twice as many as the sampling frequency of 13.5 MHz of the luminance signal (Y).

In this embodiment, over an effective image-period of a horizontal scanning line, the sampling of the digital luminance signals (Y) is carried out 720 times, and each of the samplings of the respective color-difference signals ($C_r$ and $C_b$) is carried out 360 times. Namely, a total sampling number of 1,440 (720+2×360) of the digital signals (Y, $C_r$, and $C_b$) is obtained from the effective image-period of the horizontal scanning line.

Figure 3:
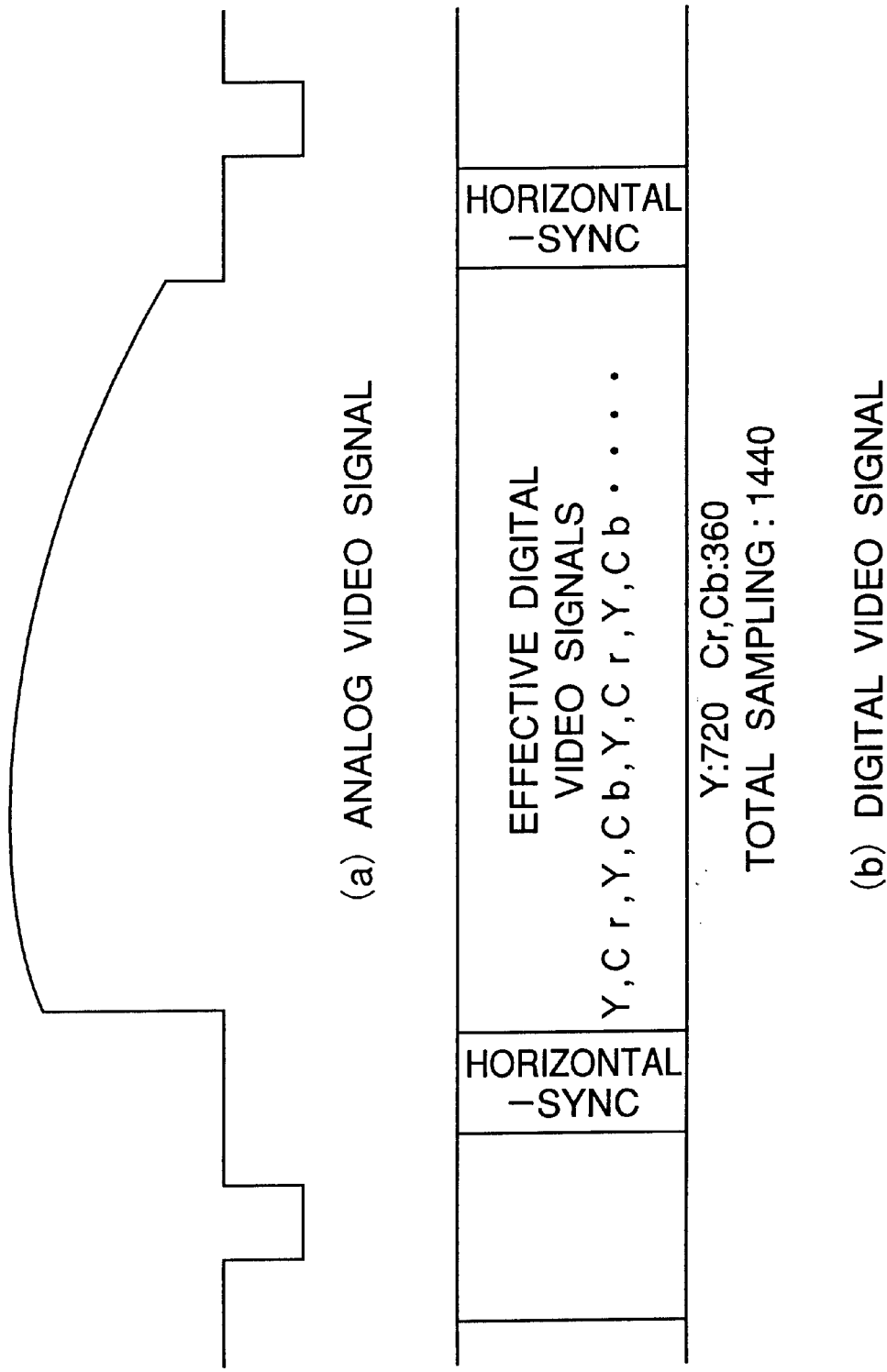
FIG. 3 is a conceptual view showing a relationship between an analog video signal of a horizontal scanning line and sampled digital signals obtained therefrom.

With reference to FIG. 3, a relationship between an analog video signal of a horizontal scanning line and sampled digital signals (Y, $C_r$, and $C_b$) obtained therefrom is conceptually shown.

If the 10-bit digital signal (Y, $C_r$, $C_b$) are directly fed from the multiplexer 24 to a peripheral equipment, the video-signal processing device and the peripheral equipment must be connected to each other through a signal cable having at least eleven signal lines. Note, ten signal lines of the signal cable are used for the feeding of the 10-bit digital signal (Y, $C_r$, $C_b$), and the other single line thereof is necessary for feeding a series of clock pulses. Of course, use of the signal cable having at least eleven signal lines is not preferable, especially, when the peripheral equipment is not placed in site, i.e., when the peripheral equipment is remote from the place at which the electronic endoscope is used, because the signal cable having a plurality of signal lines is expensive.

According to the present invention, the parallel 10-bit digital signal (Y, $C_r$, $C_b$) outputted from the multiplexer 24 is inputted to the parallel-to-serial (P/S) converter 26, which converts the parallel 10-bit digital signal (Y, $C_r$, $C_b$) into a serial 10-bit digital signal in accordance with a series of driving clock pulses having a given frequency and outputted from the timing generator circuit $20_1$.

Figure 4:
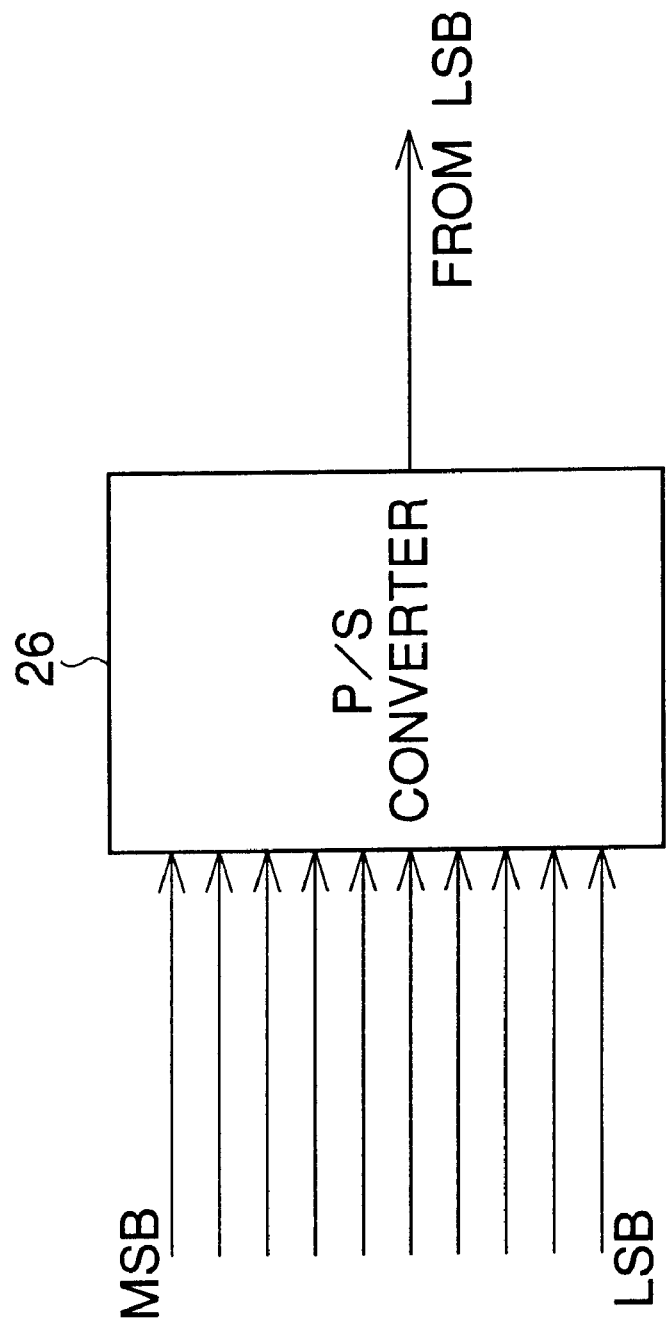
FIG. 4 is a block diagram showing a parallel-to-serial converter used in a digital-conversion processing circuit of the block diagram of FIG. 2.

As shown in FIG. 4, the conversion of the parallel 10-bit digital signal to the serial 10-bit digital signal is carried out in order from the least significant bit (LSD) to the most significant bit (MSD). Namely, the serial 10-bit digital signal is outputted from the P/S converter 26 in such a manner that the least significant bit (LSD) and the most significant bit are defined as a leading bit and a trailing bit, respectively.

Figure 5:
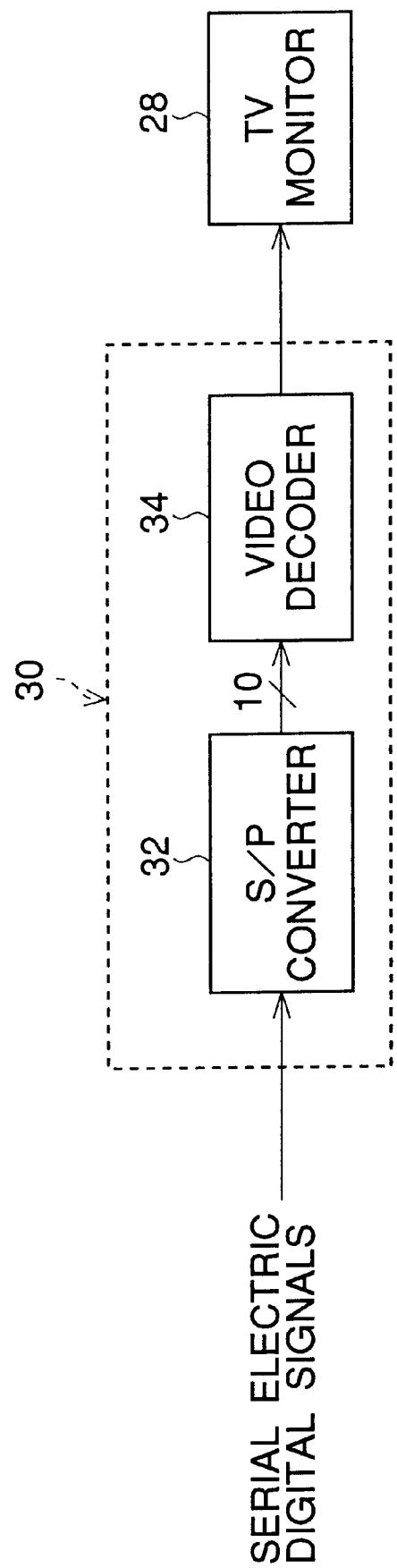
FIG. 5 is a block diagram of an analog-conversion processing device of a TV monitor to be connected to the video-signal processing device of FIG. 2.

FIG. 5 shows a TV monitor 28 as a peripheral equipment, for example, installed at a monitor center of a hospital, and the TV monitor 28 is intended to be connected to the P/S converter 26 of the digital-conversion processing circuit 18 of the video-signal processing device according to the present invention. The TV monitor 28 is provided with an analog-conversion processing circuit 30, in which the respective serial digital signals (Y, $C_r$, and $C_b$) fed from the P/S converter 26 thereto are converted into an analog red video signal (R), an analog green video signal (G), and an analog blue video signal (B).

Figure 6:
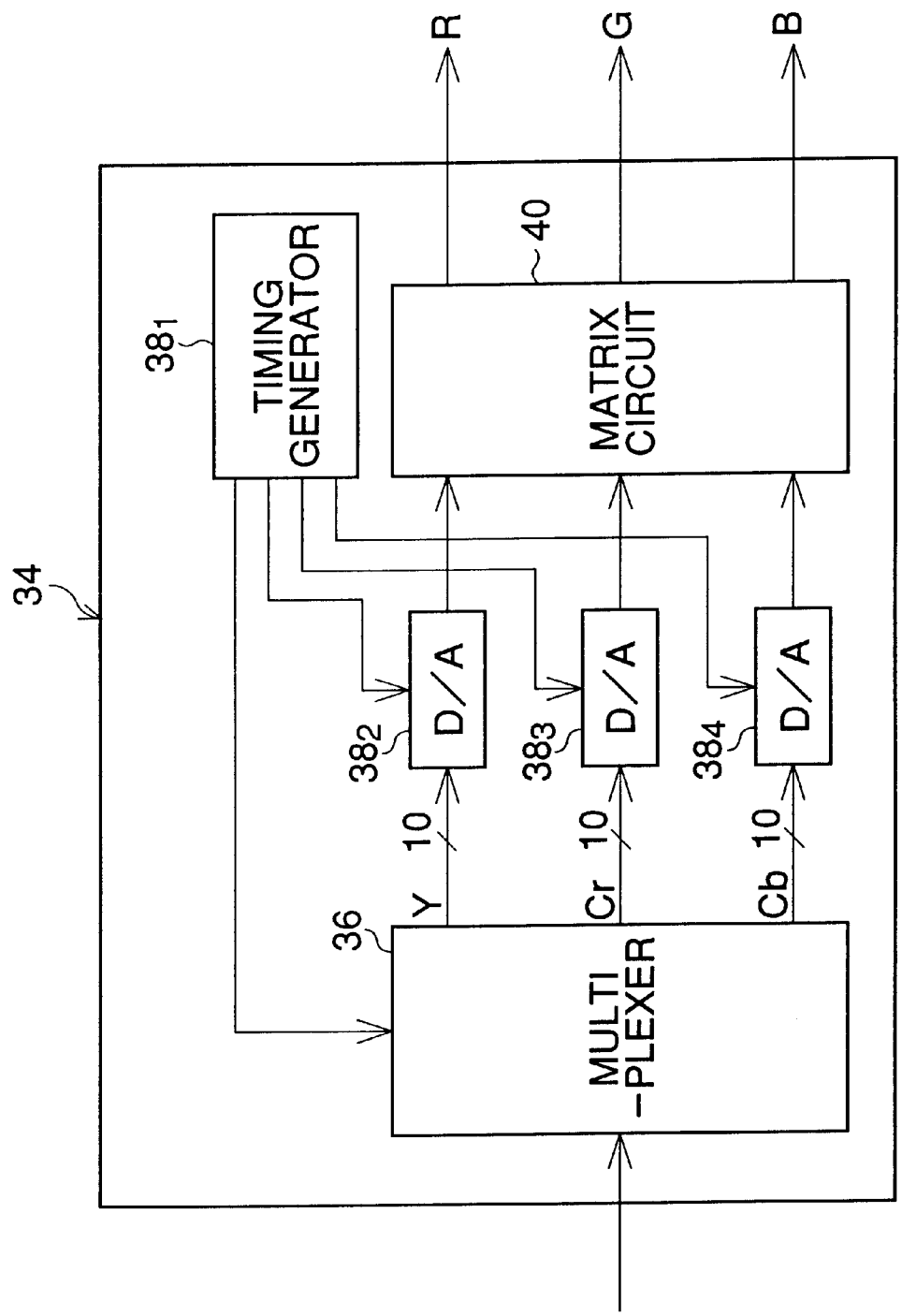
FIG. 6 is a block diagram of a video encoder included in the analog-conversion processing circuit of FIG. 5.

As shown in FIG. 5, the analog-conversion processing circuit 30 comprises a serial-to-parallel (S/P) converter 32, and a video decoder 34, and, as shown in FIG. 6, the video decoder 34 includes: a multiplexer 36; a timing generator circuit $38_1$; a digital-to-analog (D/A) converters $38_2$, $38_3$, and $38_4$; and a color-conversion matrix circuit 40.

As it is apparent from the foregoing, the serial 10-bit digital signals (Y, $C_r$, and $C_b$) are sequentially fed from the P/S converter 26 to the analog-conversion processing circuit 30 in the order of the serial 10-bit digital luminance signal (Y), the serial 10-bit color-difference signal ($C_r$), the serial 10-bit digital luminance signal (Y), and the serial 10-bit digital color-difference signal ($C_b$). The serial 10-bit digital signal (Y, $C_r$, $C_b$) fed to the analog-conversion processing circuit 30 is inputted to the S/P converter 32, which converts the serial 10-bit digital signal (Y, $C_r$, $C_b$) into the parallel 10-bit digital signal (Y, $C_r$, $C_b$).

The parallel 10-bit digital signals (Y, $C_r$, and $C_b$) outputted from the S/P converter 32 are inputted to the multiplexer 36, which distributes the 10-bit digital signals (Y, $C_r$, and $C_b$) to the D/A converters $38_2$, $38_3$, and $38_4$ in such a manner that the respective 10-bit luminance signal (Y), 10-bit color-difference signal ($C_r$), and 10-bit color-difference signal ($C_b$) are inputted to the D/A converters $38_2$, $38_3$, and $38_4$. The distribution of the 10-bit digital signals (Y, $C_r$, and $C_b$) to the D/A converters $38_2$, $38_3$, and $38_4$ is carried out in accordance with a series of clock pulses having a given frequency, which is outputted from the timing generator circuit $28_1$.

The respective D/A converters $38_2$, $38_3$, and $38_4$ convert the 10-bit digital signals (Y, $C_r$, $C_b$) into an analog luminance signal (Y), an analog color-difference signal ($C_r$), and an analog color-difference signal ($C_b$), and the conversion of each 10-bit digital signal (Y, $C_r$, $C_b$) into the analog signal is carried out in accordance with a series of clock pulses having a given frequency, which is outputted from the timing generator circuit $38_1$ to the D/A converter $38_2$, $38_3$, $38_4$.

The analog signals (Y, $C_r$, and $C_b$) outputted from the respective D/A converters $38_2$, $38_3$, and $38_4$ are inputted to the color-conversion matrix circuit 40, in which the analog signals (Y, $C_r$, and $C_b$) are converted into an analog red vide signal (R), an analog green video signal (G), and an analog blue video signal (B). These analog color video signals (R, G, and B) are fed from the color-conversion matrix circuit 40 to the TV monitor 28 to thereby reproduce a color image thereon.

Before the reproduction of the color image can be properly carried out on the TV monitor 28, a phase of the outputting frequency of the serial 10-bit digital signal (Y, $C_r$, $C_b$), i.e., a phase of the driving clock pulses for the P/S converter 26 must be coincided with a phase of the composite synchronizing signal (SYNC). To this end, the timing generator circuit $20_1$ is provided with a phase-locked loop (PLL) circuit 42 provided therein.

Figure 7:
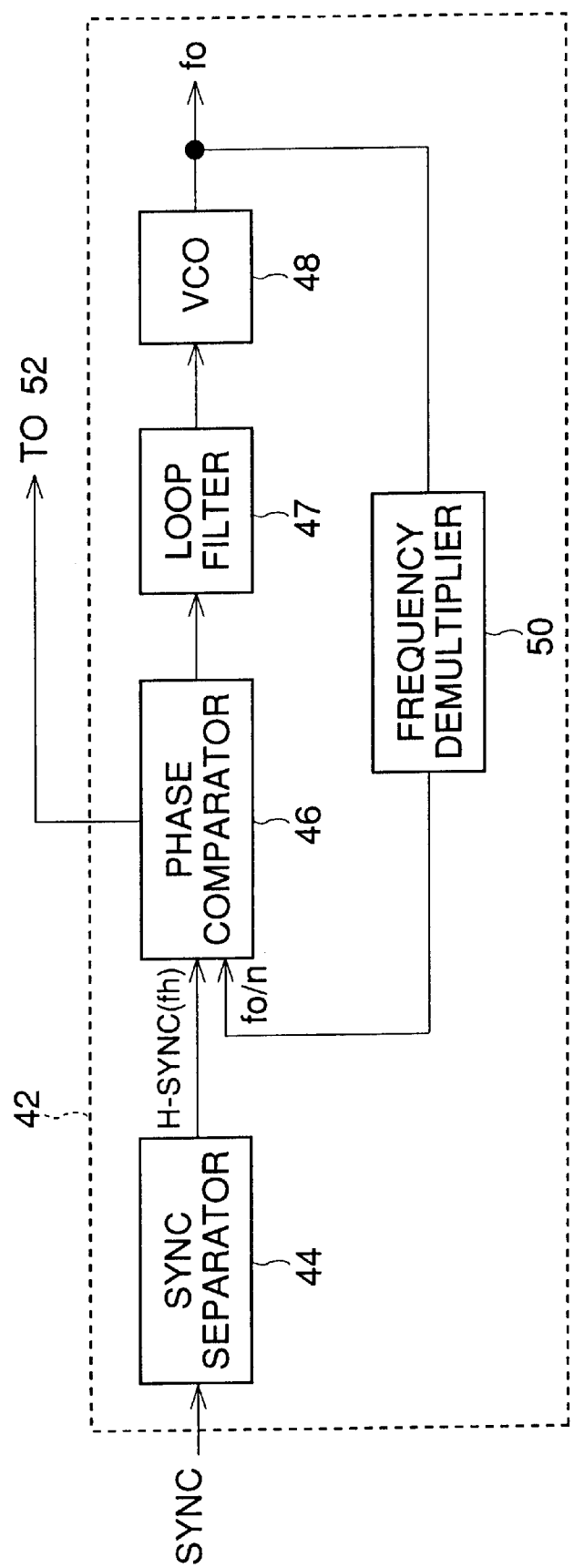
FIG. 7 is a block diagram of a phase-locked loop circuit included in a timing generator circuit shown in FIG. 2.

As shown in FIG. 7, the PLL circuit 42 includes a composite-synchronizing-signal separator 44; a phase comparator 46; a loop filter 47; a voltage controlled oscillator (VCO) 48; and a frequency demultiplier 50. The amplified composite synchronizing signal (SYNC) outputted from the amplifier $16_1$ is inputted to the composite-synchronizing separator 44, in which a horizontal synchronizing signal (H-SYNC) having a given frequency ($f_h$) is separated from the composite synchronizing signal (SYNC). Then, the separated horizontal synchronizing signal (H-SYNC) having the frequency ($f_h$) is inputted to the phase comparator 46.

On the other hand, the VCO circuit 48 outputs a series of clock pulses having a given frequency ($f_0$), which is divided by the frequency demultiplier 50 into a series of clock pulses having a frequency ($f_0/n$). Note, herein: "n" is a suitable integer. Then, the series of divided clock pulses having the frequency ($f_0/n$) is inputted to the phase comparator 46.

At the phase comparator 46, the frequency ($f_h$) of the horizontal synchronizing signal (H-SYNC) is compared with the frequency ($f_0$) of the clock pulses, and a difference between the frequencies ($f_h$ and $f_0$) is outputted from the phase comparator 46 as a voltage signal representing a phase difference between the horizontal synchronizing signal (H-SYNC) and the divided clock pulses having the frequency ($f_0/n$). Then, the voltage signal is inputted to the loop filter 47, in which the voltage signal is filtered so as to eliminate high-frequency frequency noises therefrom.

The filtered voltage signal is inputted to the VCO 48, in which the frequency ($f_0$) of the clock pulses outputted therefrom is changed on the basis of the inputted voltage signal in such a manner that the difference between the frequency ($f_h$) of the horizontal synchronizing signal and the frequency ($f_0/n$) of the divided clock pulses becomes smaller. Thus, when a level of the voltage signal outputted from the phase comparator 46 becomes zero, the phase of the clock pulses outputted from the VCO 48 is coincided with the phase of the horizontal synchronizing signal (H-SYNC), and the frequency ($f_0$) thereof is n (integer) times as many as the frequency ($f_h$) of the horizontal synchronizing signal (H-SYNC).

Note, if the NTSC color system is introduced in the electronic endoscope, the integer "n" is equal to "1,716", and if the PAL color system is introduced in the electronic endoscope, the integer "n" is equal to "1,782".

The series of clock pulses outputted from the VCO 48 and having the phase coincided with the phase of the horizontal synchronizing signal (H-SYNC) is inputted to the P/S converter 26 as the driving clock pulses for the operation thereof. In particular, the series of clock pulses inputted to the P/S converter 26 is further divided into a series of clock pulses having a frequency which is 10×n times as many as the frequency ($f_h$) of the horizontal synchronizing signal (H-SYNC), and the conversion of the parallel 10-bit digital signal (Y, $C_r$, $C_b$) into the serial 10-bit digital signal is carried out on the basis of the series of clock pulses having the frequency which is 10×n times as many as the frequency ($f_h$) of the horizontal synchronizing signal (H-SYNC), due to the serial feeding of the 10-bit digital signal (Y, $C_r$, $C_b$). Thus, the proper reproduction of the color image on the TV monitor 28 can be ensured.

As it is apparent from FIGS. 2 and 7, the phase comparator 46 is connected to a phase-lock detection circuit 52, by which it is monitored whether or not the level of the voltage signal outputted from the phase comparator 46 becomes zero. Namely, the phase-lock detection circuit 52 detects a phase-lock, i.e., a coincidence of the phase of the divided clock pulses with the phase of the horizontal synchronizing signal (H-SYNC). For example, when the level of the voltage signal outputted from the phase comparator 46 becomes zero, i.e., when the phase-lock is obtained in the phase comparator 46, a phase-lock voltage signal outputted from the phase comparator 46 to the phase-lock detection circuit 52 is changed from a low level to a high level.

As shown in FIG. 2, the phase-lock detection circuit 52 is connected to a signal-output control circuit 54, and a detection voltage signal is outputted from the phase-lock detection circuit 52 to the signal-output control circuit 54. When the phase-lock detection circuit 52 detects the change of the phase-lock voltage signal from the low level to the high level, it changes the detection voltage signal from a low level to a high level.

The signal-output control circuit 54 is connected to the P/S converter 26, and a disenabling/enabling voltage signal is outputted from the signal-output control circuit 54 to the P/S converter 26. When the detection voltage signal outputted from the phase-lock detection circuit 52 to the signal-output control circuit 54 is changed from the low level to the high level, the disenabling/enabling voltage signal is also changed from a low level to a high level.

In short, while the phase-lock detection circuit 52 does not detect the phase-lock, the disenabling/enabling voltage signal is kept at the low level, and, while the phase-lock detection circuit 52 detects the phase-lock, the disenabling/enabling voltage signal is kept at the low level.

While the disenabling/enabling voltage signal is kept at the low level, the operation of the P/S converter 26 is disenabled, whereby the P/S converter 26 outputs no serial digital signal. Namely, only while the disenabling/enabling voltage signal is kept at the high level, the operation of the P/S converter 26 is enabled, whereby the P/S converter 26 can output the serial digital signal ($Y$, $C_r$, $C_b$). Accordingly, a turbulent image cannot be reproduced on the TV monitor 28, because the serial digital signals ($Y$, $C_r$, and $C_b$) cannot be fed to the TV monitor 28 until the phase of the driving clock pulses for the P/S converter 26 is coincided with the phase of the horizontal synchronizing signal (H-SYNC). Also, even when the video-signal processing device is connected to the electronic endoscope in such a manner that the connection between the signal lines for the composite synchronizing signal (SYNC) is established after the connections between the respective red, green, and blue video signal lines for the red video signal (R), green video signal (G), and blue video signal (B) are established, a turbulent image cannot be reproduced on the TV monitor 28.

As shown in FIG. 2, the video-signal processing device is also arranged such that the first kind of analog color video signal composed of the composite synchronizing signal (SYNC), red video signal (R), green video signal (G), and blue video signal (B) is fed to a suitable peripheral equipment. Namely, the analog composite synchronizing signal (SYNC) amplified by the amplifier $16_1$ is directly outputted from the video-signal processing device, and the analog red vide signal, green video signal, and blue video signal are outputted from the video-signal processing device through a switch circuit 56 provided therein. The switch circuit 56 is connected to the signal-output control circuit 54, which caries out ON/OFF control of the switch circuit 56 on the basis of a detection voltage signal outputted from a synchronizing-signal detection circuit 58 connected to the output side of the amplifier $16_1$.

In particular, when the outputting of the composite synchronizing signal from the amplifier $16_1$ is detected by the synchronizing-signal detection circuit 58, the detection voltage signal outputted from the synchronizing-signal detection circuit 58 to the signal-output control circuit 54 is changed from a low level to a high level. At this time, an ON/OFF control voltage signal outputted from the signal-output control circuit 54 to the switch circuit 56 is also changed from a low level to a high level.

While the ON/OFF control voltage signal is kept at the low level, the switch circuit 56 is turned OFF, whereby the outputting of the analog red video signal, green video signal, and blue video signal from the video-signal processing device is disenabled. While the ON/OFF control voltage signal is kept at the high level, the switch circuit 56 is turned ON, whereby enabling the outputting of the analog red video signal, green video signal, and blue video signal from the video-signal processing device.

Accordingly, when the video-signal processing device is connected to the electronic endoscope in such a manner that the connection between the signal lines for the composite synchronizing signal (SYNC) is established after the connections between the respective red, green, and blue video signal lines for the red video signal (R), green video signal (G), and blue video signal (B) are established, the feeding of uncontrollable video signals from the video-signal processor device to a peripheral equipment is securely prevented.

As it is apparent from FIG. 2, the respective luminance signal and amplitude-modulated (AM) color-difference signal outputted from the photo-couplers $14_6$ and $14_7$ are amplified by the amplifiers $16_6$ and $14_7$, and the amplified signals are directly outputted, as the S-video signal, from the video-signal processing device to a suitable peripheral equipment connected thereto.

Also, the composite color video signal outputted from the photo-coupler $14_5$ is amplified by the amplifier $16_5$, and the amplified composite color video signal is directly outputted from the video-signal processing device to a suitable peripheral equipment.

Figure 8:
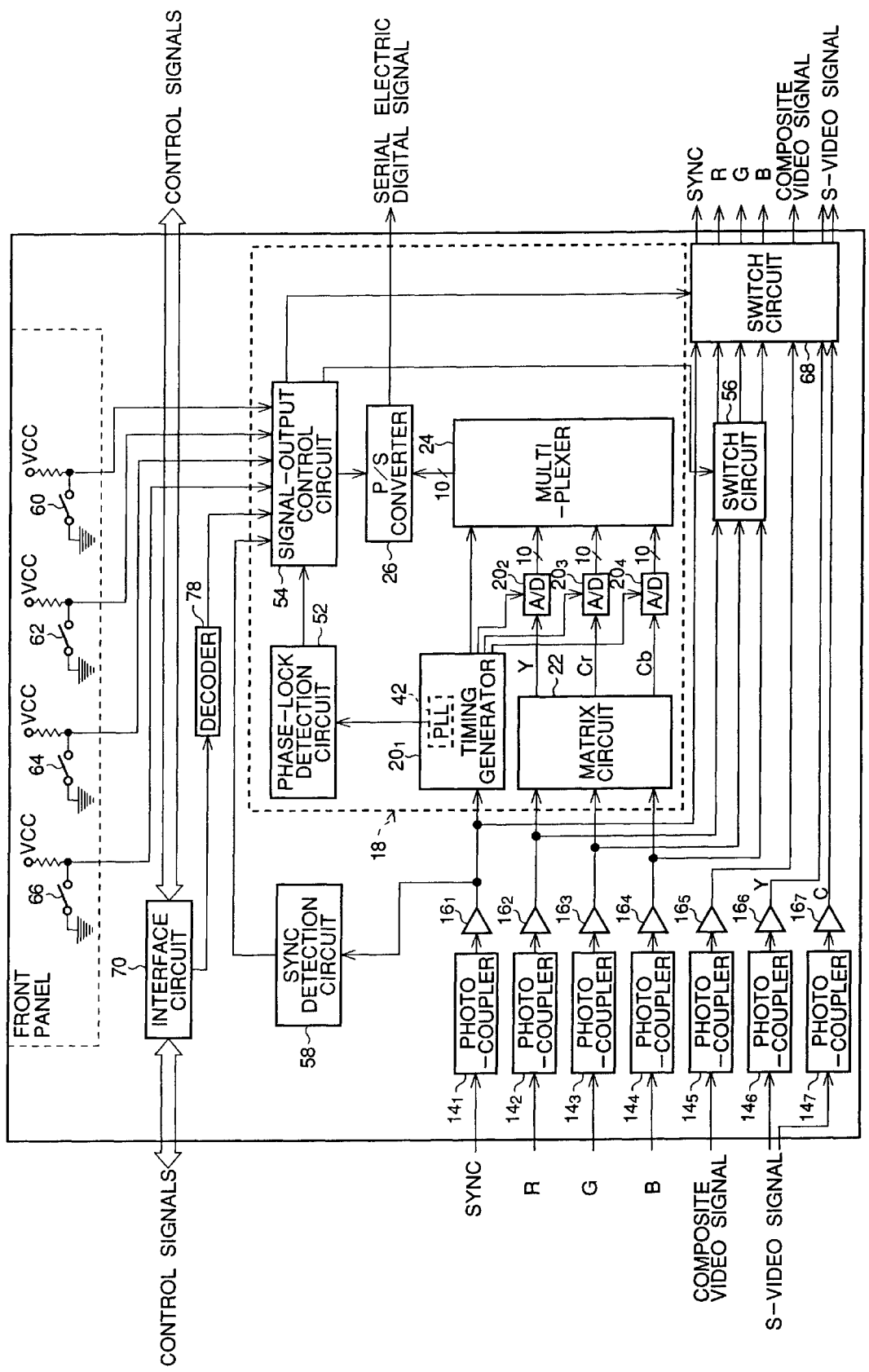
FIG. 8 is a block diagram showing a second embodiment of the video-signal processing device according to the present invention.

FIG. 8 shows a block diagram of a second embodiment of the video-signal processing device according to the present invention. In this drawing, the features similar to those of FIG. 2 are indicated by the same references.

In the second embodiment, the video-signal processing device is provided with four switches 60 to 66 provided on a front panel thereof, and each of the switches 60 to 66 is manually operated by a user, for example, a doctor. As illustrated, a first terminal end of each switches 60 to 66 is connected to the signal-output control circuit 54, and a second terminal end thereof is grounded. A voltage (VCC) is applied to the first terminal end of each switches 60 to 66. When each of the switches 60 to 66 is manually closed, the potential (VCC) of the first terminal end thereof is dropped to the ground level.

When the switch 60 is closed to thereby drop the potential (VCC) of the first terminal end thereof to the grounded level, the disenabling/enabling voltage signal outputted from the signal-output control circuit 54 to the P/S converter 26 is forcibly changed from the high level to the low level even if the phase of the driving clock pulses for the P/S converter 26 is coincided with the phase of the horizontal synchronizing signal (H-SYNC). Namely, the feeding of the serial digital signals ($Y$, $C_r$, and $C_b$) from the P/S converter 26 to the TV monitor 28 can be forcibly stopped, if necessary. For example when a user, a doctor, considers a reproduction of a photographed image on the outside TV monitor 28 undesirable, the switch 60 can be closed by him.

Each of the remaining switches 62 to 66 operates a switch circuit 68 through the intermediary of the signal-output control circuit 54, and the switch circuit 68 is provided in the signal lines for the component-type color video signal composed of the composite synchronizing signal, red video signal, green video signal, and blue video signal; the S-video signal composed of the luminance signal and amplitude-modulated (AM) color-difference signal; and the composite color video combined with the luminance signal and amplitude-modulated color-difference signal.

When the switch 62 is closed to thereby drop the potential (VCC) of the first terminal end thereof to the grounded level, the signal output control circuit 54 operates the switch circuit 68 such that the feeding of the composite synchronizing signal (SYNC), red video signal, green video signal, and blue video signal to a peripheral equipment is forcibly stopped even when the phase of the driving clock pulses for the P/S converter 26 is coincided with the phase of the horizontal synchronizing signal (H-SYNC).

Also, when the switch 64 is closed to thereby drop the potential (VCC) of the first terminal end thereof to the grounded level, the signal output control circuit 54 operates the switch circuit 68 such that the feeding of the luminance signal and amplitude-modulated color-difference signal to a peripheral equipment is forcibly stopped. Further, when the switch 66 is closed to thereby drop the potential (VCC) of the first terminal end thereof to the grounded level, the signal output control circuit 54 operates the switch circuit 68 such that the feeding of the composite color video signal to a peripheral equipment is forcibly stopped.

Figure 9:
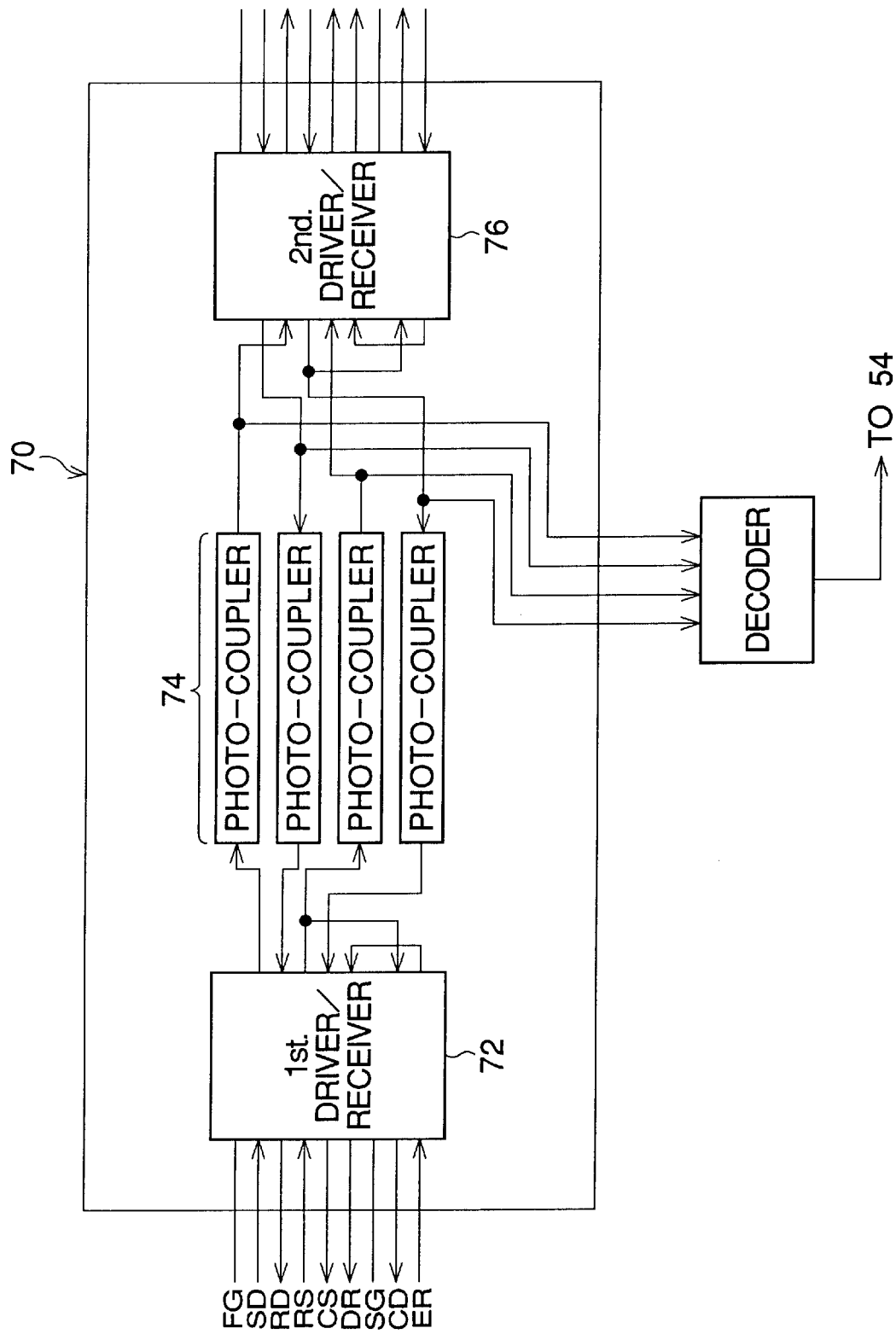
FIG. 9 is a block diagram of an interface circuit provided in the video-signal processing device of FIG. 8.

The video processor 12 of the electronic endoscope may have a plurality of input/output ports for a video-image processing computer. To this end, the second embodiment is provided with an interface circuit 70, which may be arranged as an RS-232C interface. As shown in FIG. 9, the interface circuit 70 includes: a first driver/receiver circuit 72; four photo-couplers 74; and a second driver/receiver circuit 76.

The first driver/receiver circuit 72 is connected to signal lines extended from the video processor 12 of the electronic endoscope and indicated by references (FG, SD, RD, RS, CS, RD, SG, CD, and ER). Also, the first driver/receiver circuit 72 is connected to the second driver/receiver circuit 76 through the four photo-couplers 74, and the second driver/receiver circuit 76 is connected to the video-image processing computer through signal lines corresponding to the signal lines (FG, SD, RD, RS, CS, RD, SG, CD, and ER). Accordingly, the electronic endoscope is electrically insulated from the video-image processing computer due to the existence of the photo-couplers 74.

The video-image processing computer may be placed at a place where the electronic endoscope is used, and may be installed at another place such as a monitor center of a hospital, remotely located from the place where the electronic endoscope is used. In the latter case, it is preferable to forcibly stop the feeding of the serial digital video signals (Y, $C_r$, and $C_b$) from the video-signal processing device at the monitor center side. For example, there may be a case where a connection of a TV monitor of the monitor center is changed from the video-signal processing device concerned to a video-signal processing device connected to an electronic endoscope used in another place.

To this end, the second embodiment is provided with a decoder 78 connected to the signal-output control circuit 54. When a command signal for stopping the feeding of the serial digital video signals (Y, $C_r$, and $C_b$) from the P/S converter 26 is fed from the video-image processing computer to the video-signal processing device, the command signal is inputted to the decoder 78 through the interface circuit 70. Upon inputting the command signal to the decoder 78, a voltage signal outputted from the decoder 78 to the signal-output control circuit 54 is changed from a low level to a high level, whereby the disenabling/enabling signal is forcibly changed from the high level to the low level. Thus, the feeding of the serial digital video signals (Y, $C_r$, and $C_b$) from the P/S converter 26 to the TV monitor is forcibly stopped.

The video-signal processing device as mentioned above is intervened between the electronic endoscope and various peripheral equipments such as a TV monitor, a video tape recorder, a printer, a video-image processing computer and so on. The electronic endoscope is electrically insulated from the peripheral equipments due to the existence of the photo-couplers ($14_1$ to $14_7$; 74) of the video-signal processing device according to the present invention.

According to the present invention, the serial digital video signals (Y, $C_r$, and $C_b$) outputted from the digital-conversion processing circuit 18 can be fed to the TV monitor 28 through a coaxial cable having a single signal line, which is cheaper than the signal cable having at least eleven single lines as mentioned above. Also, although the TV monitor 28 is remote from the place where the electronic endoscope is used, a clear and proper reproduction of color images on the TV monitor 28 can be ensured, because the video signal is fed to the TV monitor 28 as the digital video signal.

Figure 10:
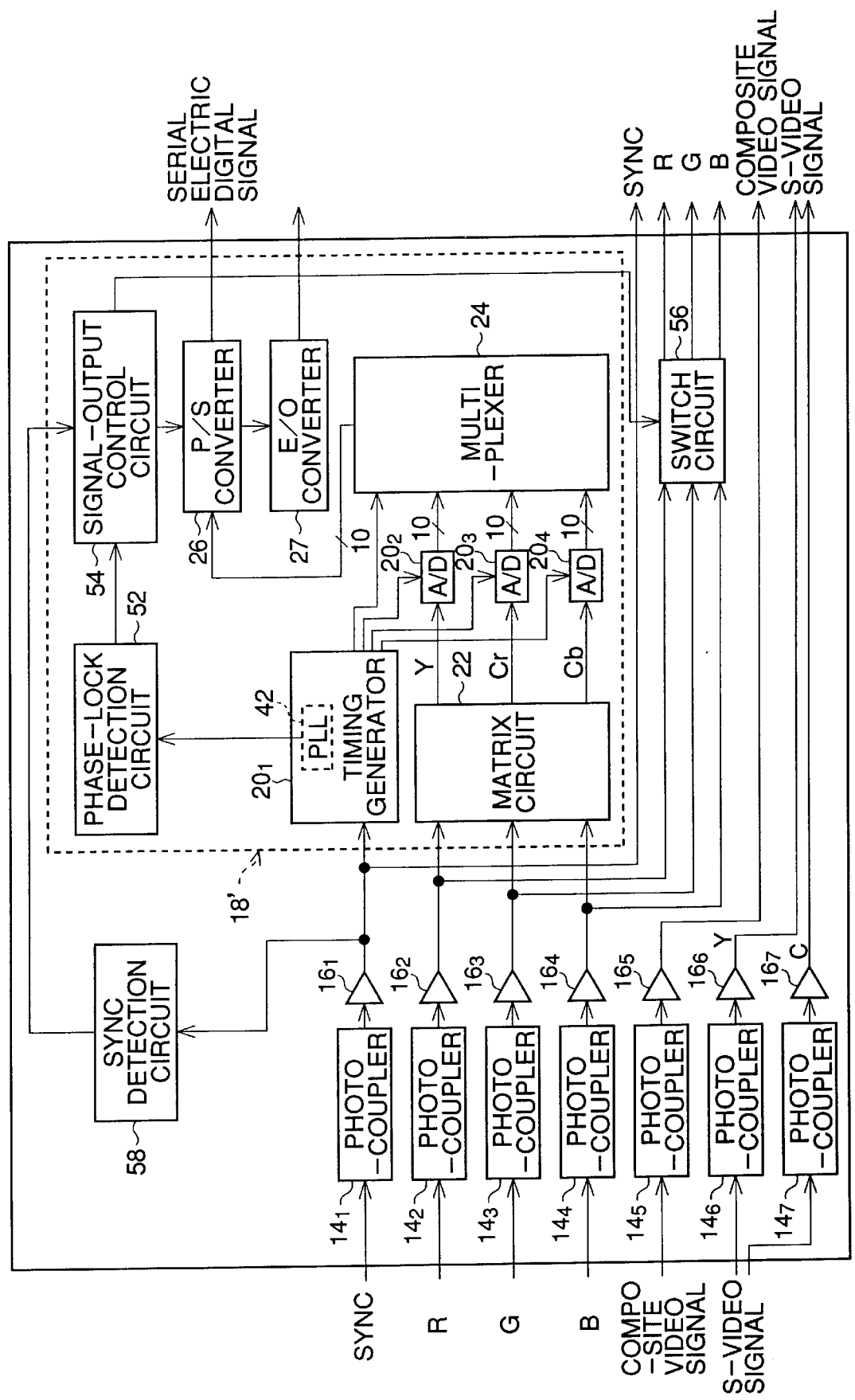
FIG. 10 is a block diagram showing a third embodiment of the video-signal processing device according to the present invention.

FIG. 10 shows a block diagram of a third embodiment of the video-signal processing device according to the present invention. In this drawing, the features similar to those of FIG. 2 are indicated by the same references. The third embodiment is identical with the first embodiment of FIG. 2 except that a digital-conversion processing circuit 18' of the former further includes an electrical-optical (E/O) converter 27 connected to the P/S converter 26, to thereby convert the respective serial electric digital signals (Y, $C_r$, and $C_b$) into serial optical digital signals (Y, $C_r$, and $C_b$). Namely, in the third embodiment, the digital-conversion processing circuit 18 can output not only the serial electric digital signals (Y, $C_r$, and $C_b$) but also the serial optical digital signals (Y, $C_r$, and $C_b$).

Figure 11:
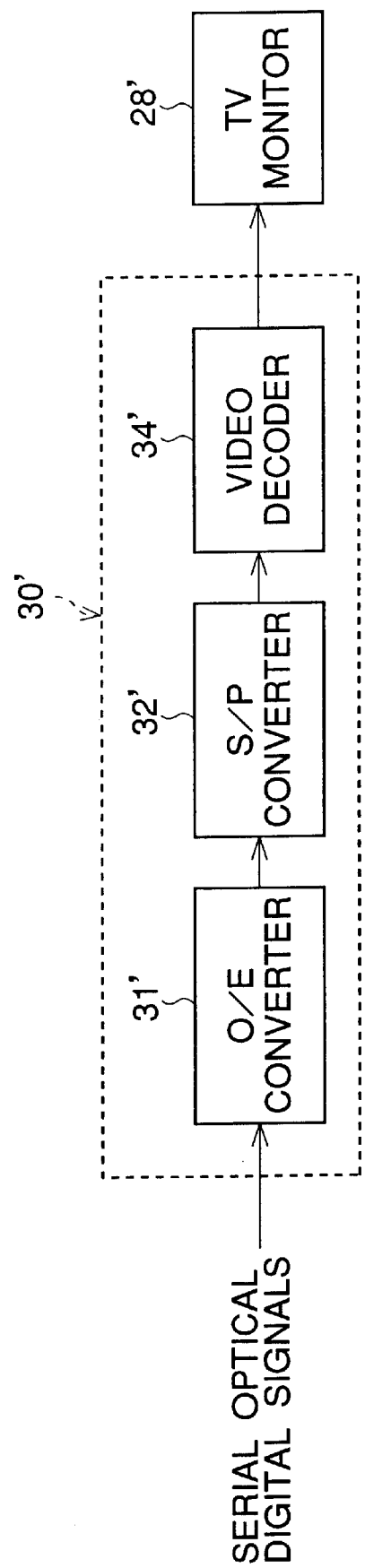
FIG. 11 is a block diagram of an analog-conversion processing circuit of a TV monitor to be connected to the video-signal processing device of FIG. 11.

FIG. 11 shows a TV monitor 28' as a peripheral equipment, which is intended to be connected to the E/O converter 27 of the digital-conversion processing circuit 18' through an optical fiber cable. To this end, the TV monitor 28' is provided with an analog-conversion processing circuit 30', in which the respective serial optical digital signals (Y, $C_r$, and $C_b$) fed from the E/O converter 27 thereto the optical fiber cable are converted into an electric analog red video signal (R), an electric analog green video signal (G), and an electric analog blue video signal (B).

As shown in FIG. 11, the analog-conversion processing circuit 30' comprises an optical-electrical (O/E) converter 31', a serial-to-parallel (S/P) converter 32', and a video decoder 34'. Note, the video decoder 34' is identical with the video decoder 34 shown in FIG. 6.

The serial optical digital signals (Y, $C_r$, and $C_b$) are sequentially fed from the E/O converter 27 to the analog-conversion processing circuit 30' in the order of the serial optical digital luminance signal (Y), the serial optical color-difference signal ($C_r$), the serial optical digital luminance signal (Y), and the serial optical digital color-difference signal ($C_b$). The serial optical digital signal (Y, $C_r$, $C_b$) fed to the analog-conversion processing circuit 30' is inputted to the O/E converter 31', which converts the serial optical digital signal (Y, $C_r$, $C_b$) into the serial electric digital signal (Y, $C_r$, $C_b$).

The serial electric digital signals (Y, $C_r$, and $C_b$) outputted from the O/E converter 31' are inputted to the S/P converter 32', which converts the serial electric digital signals (Y, $C_r$, and $C_b$) into parallel electric digital signals (Y, $C_r$, and $C_b$). These parallel digital signals (Y, $C_r$, and $C_b$) outputted from the S\P converter 32 are inputted to the video decoder 34', in which the parallel digital signals (Y, $C_r$, $C_b$) are processed as substantially the same manner as in the video decoder 34 (FIG. 6), whereby the video decoder 34' outputs an analog red vide signal (R), an analog green video signal (G), and an analog blue video signal (B) to the TV monitor 28' to thereby reproduce a color image thereon.

The optical fiber cable used to feed the serial optical digital signals (Y, $C_r$, and $C_b$) from the E/O converter 27 to the analog-conversion processing circuit 30' has a signal-feed loss lower than that of the coaxial cable used to feed the serial electric digital signals (Y, $C_r$, and $C_b$) from the P/S converter to the analog-conversion processing circuit 30 (FIG. 5). Accordingly, the third embodiment is preferred when the peripheral equipment such as the TV monitor 28', is remote from the place where the electronic endoscope is used. Also, the peripheral equipment such as the TV monitor 28' can be more securely insulated from the electronic endoscope due to the existence of the optical fiber cable therebetween.

Figure 12:
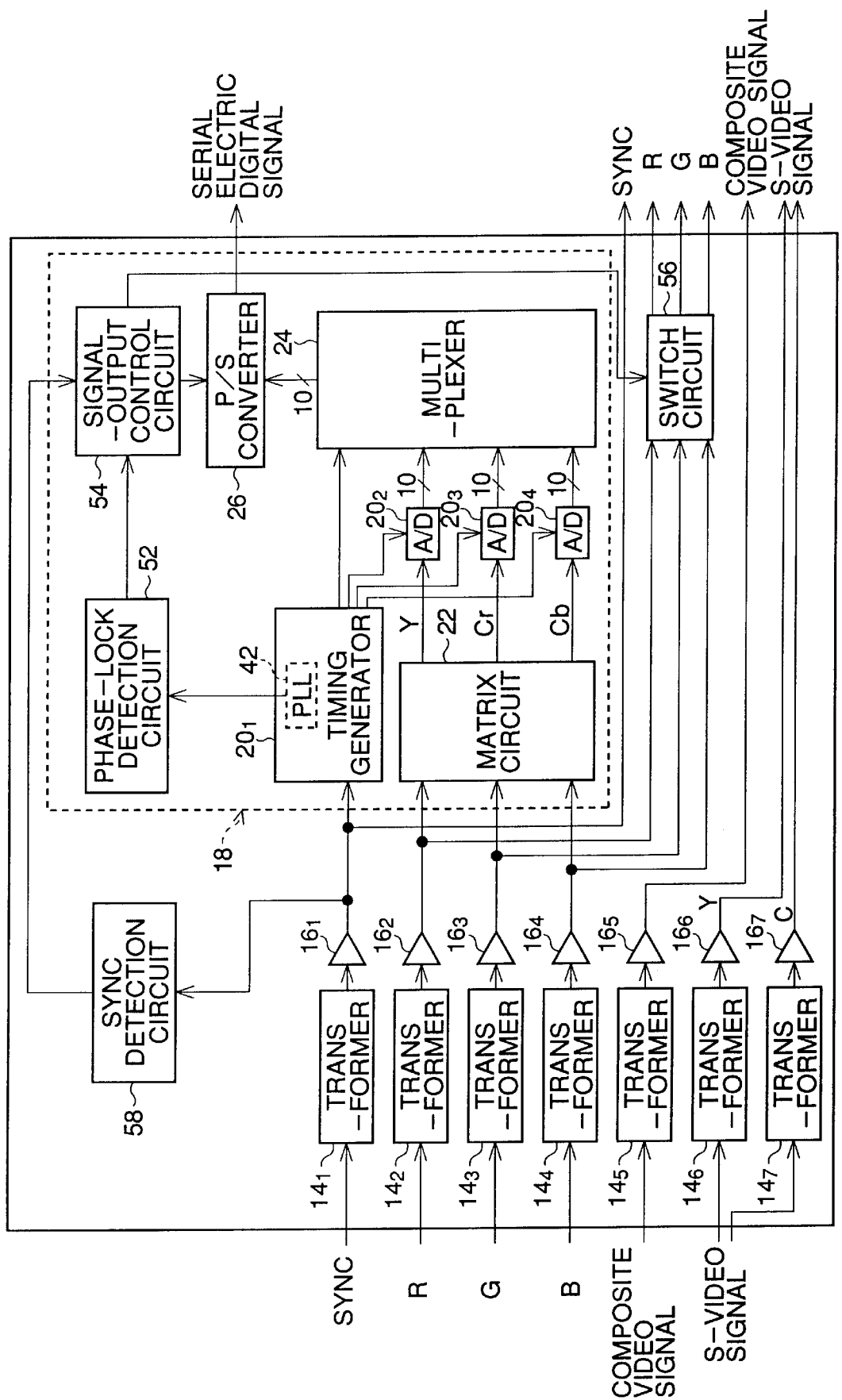
FIG. 12 is a block diagram showing a fourth embodiment of the video-signal processing device according to the present invention.

FIG. 12 shows a fourth embodiment of the video-signal processing device according to the present invention. In this drawing, the features similar to those of FIG. 2 are indicated by the same references. The forth embodiment is identical with the first embodiment of FIG. 2 except that, in a digital-conversion processing circuit 18', seven transformers $14_1'$ to $14_7'$ are substituted for the photo-couplers $14_1$ to $14_7$.

In the fourth embodiment, the respective primary windings of the transformers $14_1'$ to $14_7'$ are connected to the output lines of the video processor 12 of the electronic endoscope, and the respective secondary windings of transformers $14_1'$ to $14_7'$ are connected to the amplifiers $16_1$ to $16_7$. Thus, the electronic endoscope is electrically insulated from the video-signal processing device.

Figure 13:
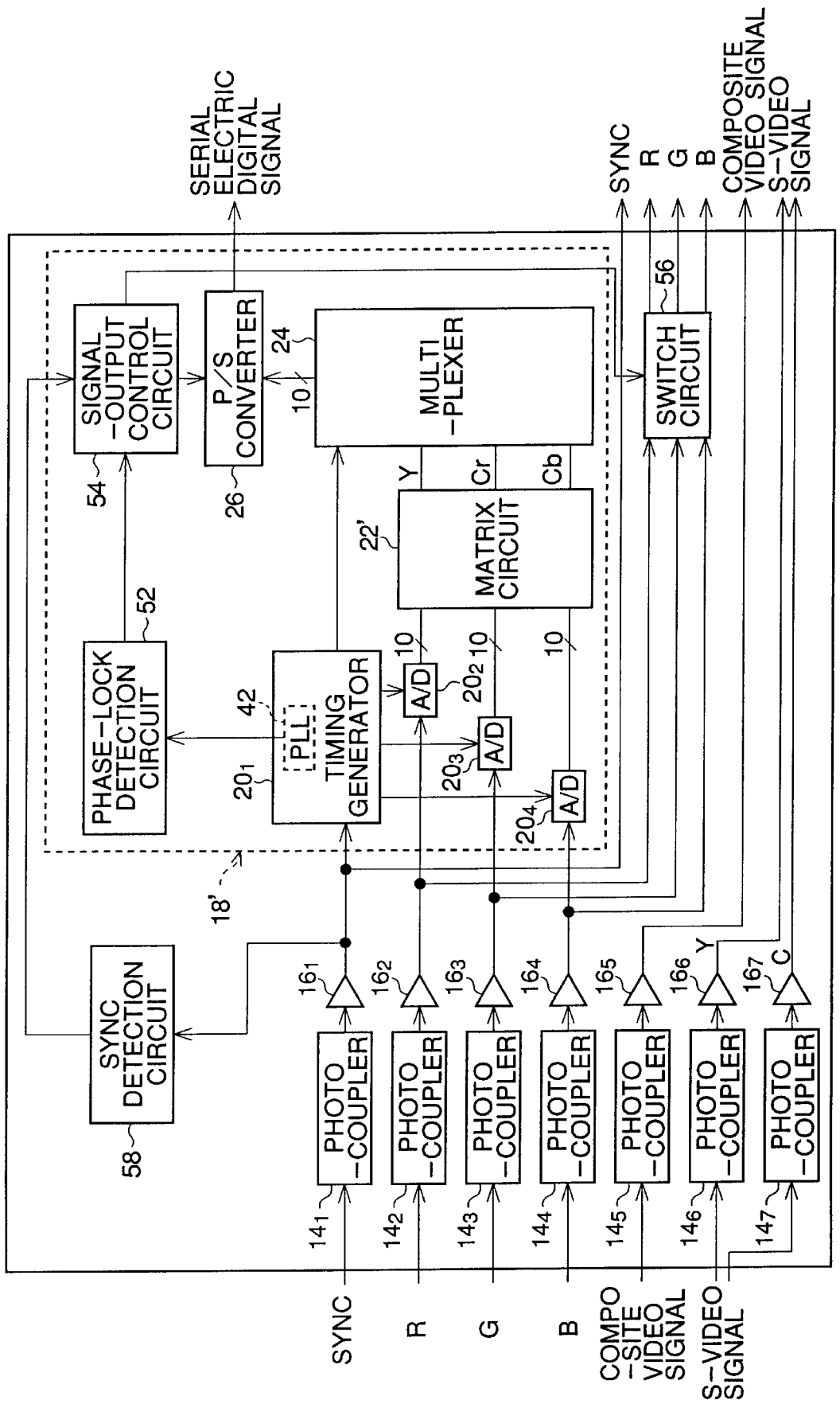
FIG. 13 is a block diagram showing a fifth embodiment of the video-signal processing device according to the present invention.

FIG. 13 shows a fifth embodiment of the video-signal processing device according to the present invention. In this drawing, the features similar to those of FIG. 2 are indicated by the same references. The fifth embodiment is identical with the first embodiment of FIG. 2 except that, in a digital-conversion processing circuit 18', a color-conversion digital matrix circuit 22' is substituted for the color-conversion analog matrix circuit 22, and is disposed between the A/D converters $20_2$ to $20_4$ and the multiplexer 24.

In the fifth embodiment, the respective red video signal (R), green vide signal (G), and blue video signal (B) outputted from the amplifiers $16_2$ to $16_4$ are inputted to the A/D converters $20_2$ to $20_4$, which converts the video signals (R, G, and B) into 10-bit digital signals (R, G, and B). Then, the respective 10-bit color digital video signal (R, G, and B) outputted from the A/D converters $20_2$ to $20_4$ are inputted to the color-conversion digital matrix circuit 22', which produces a digital luminance signal (Y), and two kinds of digital color-difference signals ($C_r$=R−Y and $C_b$=B−Y) on the basis of the inputted color digital video signals (R, G, and B). Thus, the 10-bit digital luminance signal (Y), and the two kinds of 10-bit color-difference signals ($C_r$ and $C_b$) are processed in substantially the same manner as mentioned above.

FIG. 14 shows a sixth embodiment of the video-signal processing device according to the present invention. In this drawing, the features similar to those of FIG. 2 are indicated by the same references. The sixth embodiment is identical with the first embodiment of FIG. 2 except that the color-conversion analog matrix circuit 22 is eliminated from a digital-conversion processing circuit 18'.

The sixth embodiment is connectable to the electronic endoscope which is arranged so as to output another component-type color video signal, including a luminance signal (Y), and two kinds of color-difference signals ($C_r$ and $C_b$), from the video processor thereof. Thus, in the sixth embodiment, the color-conversion analog matrix circuit (22) is unnecessary.

Finally, it will be understood by those skilled in the art that the foregoing description is of preferred embodiments of the device and that various changes and modifications may be made to the present invention without departing from the spirit and scope thereof.

The present disclosure relates to subject matter contained in Japanese Patent Applications No. 8-110269 (filed on Apr. 5, 1996), and No. 8-117086 (filed on Apr. 15, 1996), which are expressly incorporated herein, by reference, in their entireties.

What is claimed:

1. A video-signal processing device connectable to an electronic endoscope, the electronic endoscope being capable of outputting a component-type electric analog color video signal as at least one kind of video signal, the component-type electric analog color video signal comprising a composite synchronizing signal-component, a red video-signal-component, a green video-signal-component, and a blue video-signal-component, said device comprising:

an analog-to-digital converter that converts each of the red video-signal-component, the green video-signal-component, and the blue video-signal-component into a parallel digital color video-signal-component;

a color-conversion digital matrix circuit that produces a parallel digital luminance signal-component, and two kinds of parallel digital color-difference signal-components based on the parallel digital color video-signal-components;

a parallel-to-serial converter that converts the parallel digital luminance signal-component and the parallel digital color-difference signal-components into serial digital color video-signal-components in accordance with a series of clock pulses;

a phase-locked loop circuit that coincides a phase of the clock pulses with a phase of the composite synchronizing signal component of the component-type electric analog color video signal, the serial digital color video-signal-components being outputted from the device at a proper timing;

a phase-lock detector that detects the coincidence of the phase of the clock pulses with the phase of the composite synchronizing signal component; and a signal-output stopper that stops the outputting of the serial digital color video-signal-components from said device until said phase-lock detector detects the coincidence of the phase of the clock pulses with the phase of the composite synchronizing signal component.

2. The video-signal processing device as set forth in claim 1, further comprising an electrical-optical converter that converts the electric signal of the serial digital color video-signal-components into serial optical digital color video-signal components.

3. The video-signal processing device as set forth in claim 1, further comprising a manual switch that stops the outputting of the serial electric digital color video-signal-components.

4. The video-signal processing device as set forth in claim 1, further comprising an insulation coupler for inputting the component-type electric analog color video signal from the electronic endoscope to said device, whereby the electronic endoscope is electrically insulated from peripheral equipment.

5. The video-signal processing device as set forth in claim 4, wherein said insulation coupler comprises a photo-coupler.

6. The video-signal processing device as set forth in claim 4, wherein said insulation coupler comprises a transformer-coupler.

* * * * *